United States Patent [19]
Kidwell

[11] Patent Number: 5,314,802
[45] Date of Patent: May 24, 1994

[54] LIGHT EMISSION- OR ABSORBANCE-BASED BINDING ASSAYS

[75] Inventor: David A. Kidwell, Alexandria, Va.

[73] Assignee: The United States of America as represented by the Secretary of the Navy, Washington, D.C.

[21] Appl. No.: 865,526

[22] Filed: Apr. 9, 1992

[51] Int. Cl.⁵ ........................................ G01N 33/533
[52] U.S. Cl. ..................... 435/7.1; 435/7.5; 435/962; 436/512; 436/536; 436/537; 436/800
[58] Field of Search ............... 435/7.1, 962, 7.5; 436/512, 536, 537, 800, 501

[56] References Cited

U.S. PATENT DOCUMENTS 4,272,505  6/1981  Smith ..................................... 424/8

OTHER PUBLICATIONS

Avis et al. J. Chem. Soc. Faraday Trans. 2, 70(6) 1057–65 (1974).
Fucillo Biotechniques 3(6) 494–6, 498–501 (1985).
Morrison, "Time-Resolved Detection of Energy Transfer: Theory and Application to Immunoaasays," Analytical Biochemistry, 1988, pp. 101–120.
Chandross et al., "Intramolecular Excimer Formation and Fluorescence Quenching in Dinaphthylalkanes," Journal of the American Chemistry Society, 1970, pp. 3586–3593.
Cuniberti et al., "Intramolecular Excimer Formation in Polymers," European Polymer Journal vol. 16, 1980, pp. 887–893.
Patel et al., "Homogeneous Immunoassay Based on Chemiluminescence Energy Transfer," Clin. Chem. 29/9, 1604–1608, 1983.
Pohl et al., "Chromophoric and Fluorophoric Peptide Substrates Clevaed Through the Dipeptidyl Carboxypeptidase ACtivity of Cathepsin B," Analytical Biochemistry 165, 96–101, 1987.
Carmel et al., "Use of Substrates with Fluorescent Donor and Acceptor Chromophores for the Kinetic Assay of Hydrolases," North-Holland Publishing Company-Amsterdam, vol. 30 No. 1, Febs Ltrs., 1973, pp. 11–14.
Telser et al., "DNA Duplexes Covalently Labeled at Two Sites: Synthesis and Characterization by Steady-State and Time Resolved Optical Spectroscopies," J. Am. Chem. Soc., 1989, pp. 7226–7232.

Primary Examiner—Esther L. Kepplinger
Assistant Examiner—Lora M. Green
Attorney, Agent, or Firm—Thomas E. McDonnell; Barry A. Edelberg

[57] ABSTRACT

A substance having binding sites for at least two molecules may be detected within a sample. A molecule which can be recognized by the substance is labelled such that when at least two of the labelled molecules are bound the binding sites on the substance, the labels on the molecules electronically interact with each other and vary the wavelength dependance of their spectra. This variation in the spectra of the label can be detected. If the sample is suspected of containing the unlabelled form of a molecule, such as biotin or cocaine, a known amount of the above substance, along with a known amount of the corresponding labelled biotin or cocaine is added to the sample. In this instance, the amount of the suspect molecule in the sample is then determined by the extent to which the variation in the spectra of the label has been reduced. Alternatively, the present invention can be used to determine the binding characteristics of the substance within the sample. The method of the present invention is useful in immunoassays or other bioassays as well as in studies of surface interactions.

19 Claims, 12 Drawing Sheets

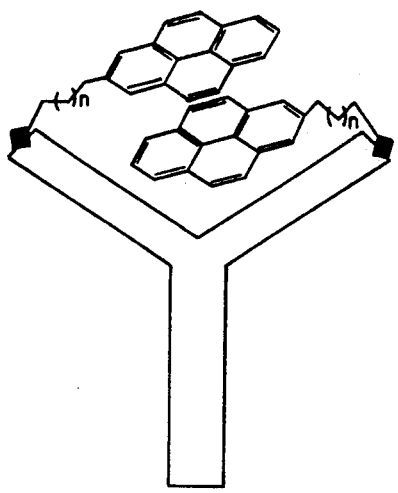 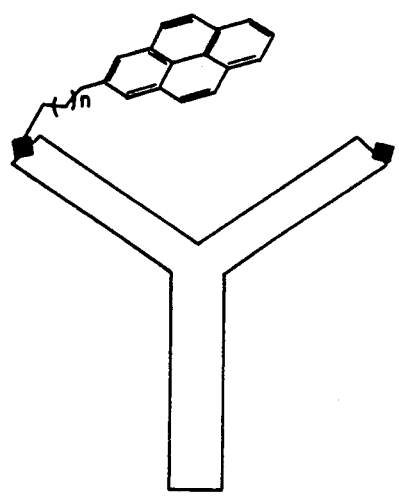
FIG. 3a  FIG. 3b
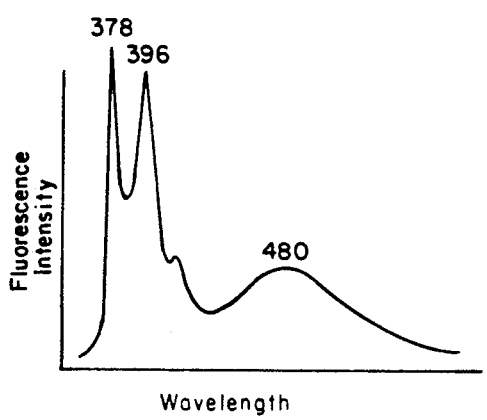 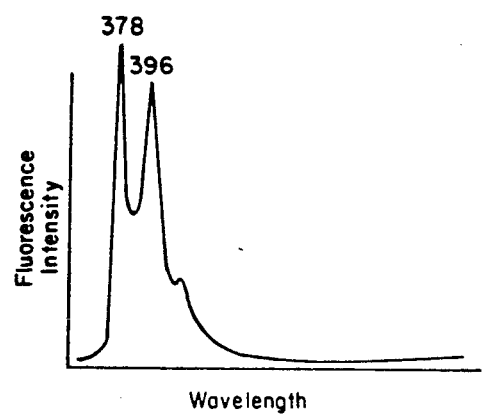
FIG. 3c  FIG. 3d

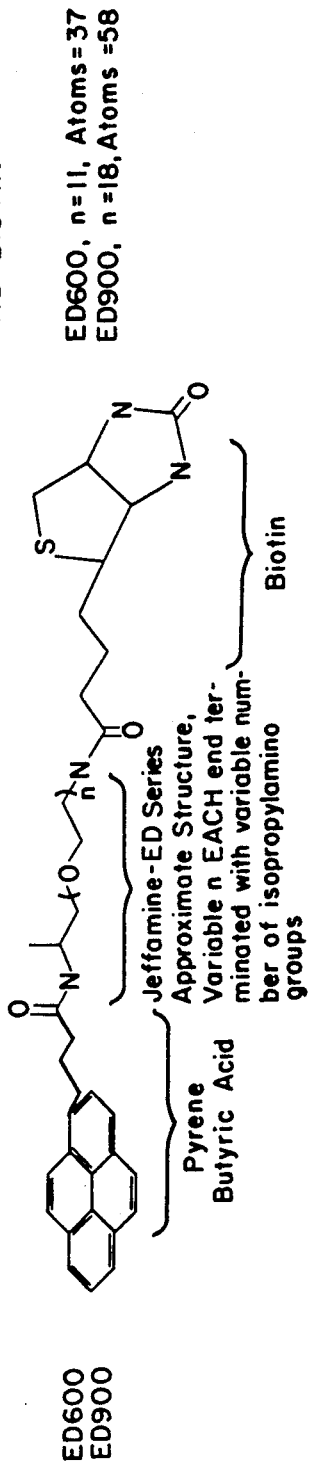
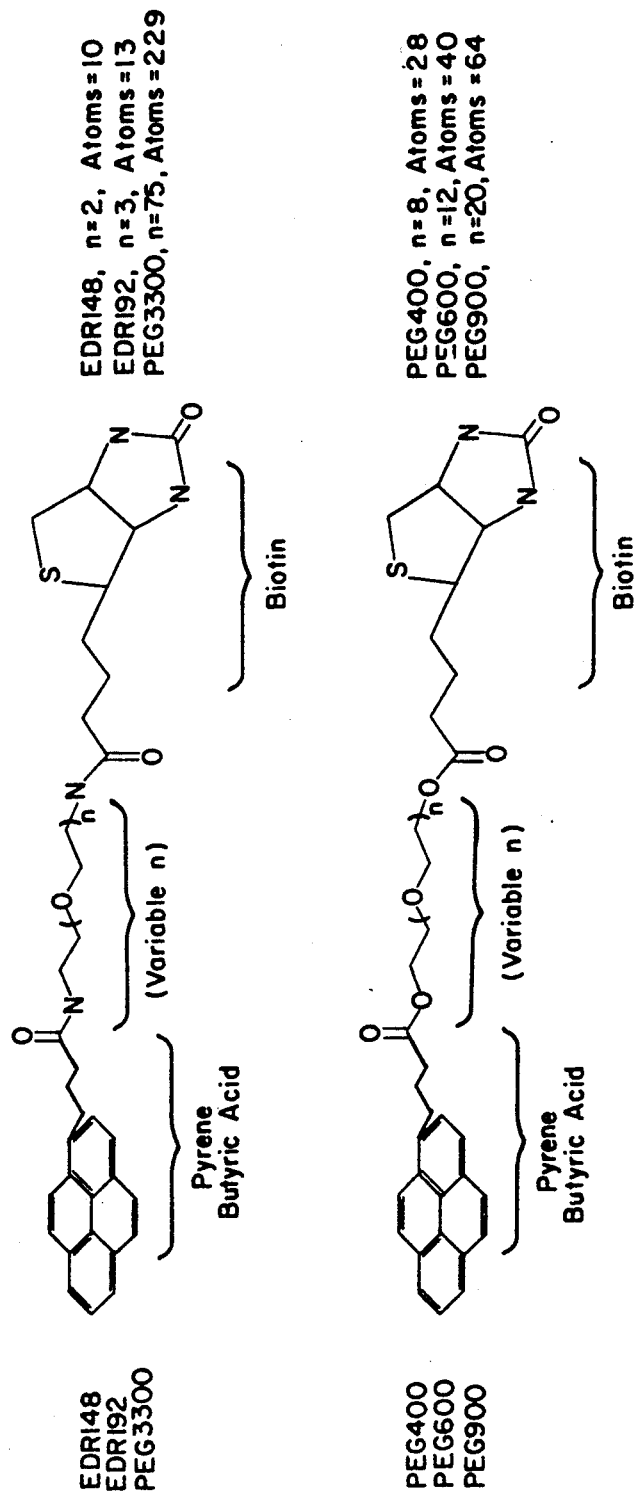
FIG. 4

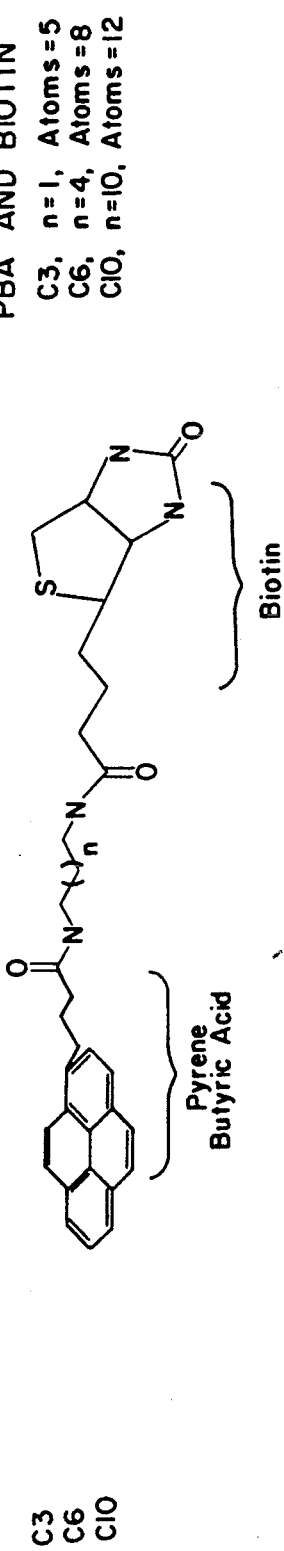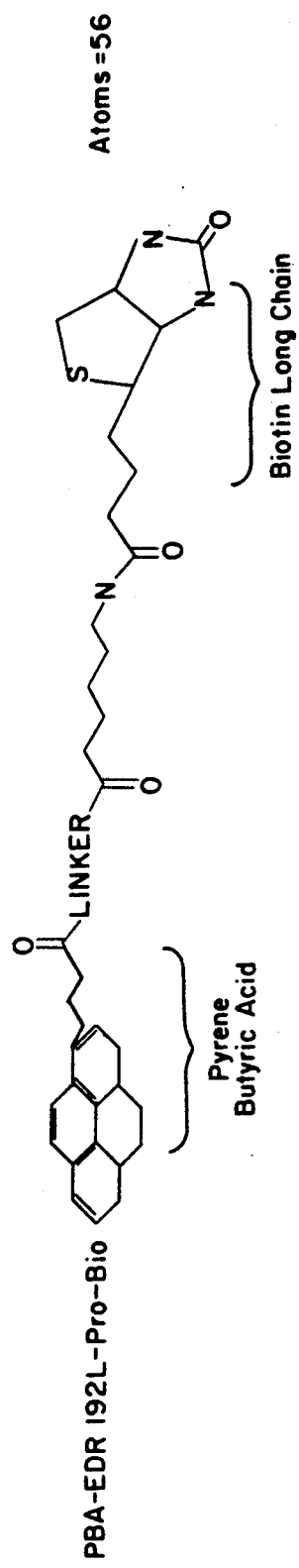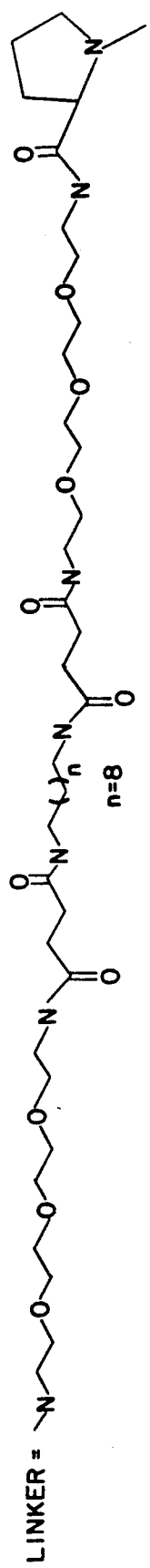
FIG. 5

LIGHT EMISSION- OR ABSORBANCE-BASED BINDING ASSAYS

BACKGROUND OF THE INVENTION

1. Field of the Invention

The present invention relates generally to assays and more specifically to light emission- or absorbance-based binding assays.

2. Background Art

Binding assays, for example, immunoassays and receptor based assays, are widely used in the medical community as diagnostic tests. There are several binding assays that have been produced and are currently on the market since the principle was developed by R. S. Yalow and S. A. Berson, *J. Clinical Investigations*, 39 1157(1960). An example of a binding assay is Radioimmunoassay (RIA) (D. Monroe, *Anal. Chem.*, 56 920A(1984)). All immunoassays exploit the binding capabilities of antibodies. However other molecules that are capable of recognizing and specifically binding other molecules may be employed. Antibodies are protein molecules which are frequently considered fighters of infections. They fight infections by binding to the infectious material in a specific manner, forming a complex. This is then a signal to the organism to reject that complex. However, antibodies may also be produced to bind to an individual compound, as a key fits a lock. To be useful in an assay, this recognition event must generate a signal that is macroscopically observable. The method employed to generate such a signal is what distinguishes the various types of immunoassays. In the above example, radioactivity is employed. RIA is quite sensitive and widely used, but the expense and restrictions for handling radioactive material makes alternative immunoassays desirable.

Fluorescence and chemiluminescence have been used in various types of assays, such as enzyme assays and immunoassays. In each of these systems, energy-coupling reactions have been exploited.

Carmel et al., FEBS Letters, Vol. 30, No. 1, February 1973, pages 11 through 14, describe the use of fluorescent donors and acceptors which are in close proximity to each other to measure the rate of enzymatic cleavage of a suitable labelled peptide. In their system, a peptide is labelled with two fluorophores. One fluorophore (the donor) accepts excitation light and fluoresces. If the other fluorophore (the acceptor) is in close proximity to the donor, it can accept the emitted light of the donor as excitation light or energy and then emit its own fluorescence. Since Förster, Ann. Physik., 2 (1948) 55, has shown that the probability of the donor exciting the acceptor decreases with the sixth power of the distance between them, if they are separated by enzymatic cleavage of the peptide linker, the fluorescence of the acceptor will decrease substantially. Thus, a measure of the fluorescent intensity of the acceptor is inversely proportional to the rate of enzymatic activity. Although such a system is quite sensitive, it is difficult to find appropriate donors and acceptors such that the donor may be exclusively excited by the incident radiation without exciting the acceptor.

Binding assays have been produced by using the donor/acceptor scheme described above. In this case, the donor is a fluorescently labelled hapten and the acceptor is the antibody with many fluorescent acceptors attached. This large concentration of fluorescent acceptors is needed because the distances are greater than in simple peptide enzymatic substrates. However, the same problems occur with finding appropriate donors and acceptors that occur with enzymatic substrates. Patel et al., Clin. Chem., Vol. 29, No. 9, 1983, 1604-1608, have overcome some of these difficulties by using chemiluminescence to excite the acceptor. To achieve the reported high sensitivities, a very sensitive instrument must be employed.

Similar systems (Pohl et al., Analytical Biochemistry 165, 96-101 (1987)) have used fluorescent quenching to measure the distance between a quencher and a fluorophore, both attached to the same peptide linker. The increase in fluorescence when the peptide linker is cleaved is a measure of the enzymatic activity. However, the quencher is not very efficient in reducing fluorescent such that only a five- to eight-fold increase in fluorescence is observed when the peptide linker is cleaved.

Among the numerous binding assays that are possible, the one of most interest is that for detection of small molecular weight species. For immunoassays, i.e., use of an antibody as the binding molecule, this type of binding assay is termed a competition immunoassay.

SUMMARY OF THE INVENTION

Accordingly, it is an object of this invention to provide a binding assay where no separation steps are necessary for measurement.

It is another object of the present invention to provide an amplification scheme which is not subject to decrease in activity over time in storage, as are assays using radioactivity or enzymes.

It is a further object of the present invention to replace radioactivity with an environmentally safer detection scheme, yet, at least in some embodiments, maintain the sensitivity that radioactivity permits.

These and additional objects of the invention are accomplished by replacing radioactivity with a fluorescent molecule, such as pyrene, which shows a change in spectra with concentration.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein:

FIGS. 3a through 3d show stylized fluorescence spectra (FIGS. 3c and 3d), and the stylized structure of, pyrene-labelled hapten where no unlabelled hapten is present (FIGS. 3a and 3c) and where labelled hapten is present (FIGS. 3b and 3d), respectively.

FIG. 4 is a table showing representative structures of some of the linker arms employed and their code names.

FIG. 5 is a table showing additional representative structures of some of the linker arms employed and their code names.

DETAILED DESCRIPTION OF THE PREFERRED EMBODIMENT

In the present disclosure and claims, binding assays are defined as assays using molecules, molecular complexes or surfaces that selectively bind two or more other molecules. This definition encompasses but is not limited to antibodies, antibody fragments, streptavidin, avidin, receptors and lectins and surfaces.

Figure 1:
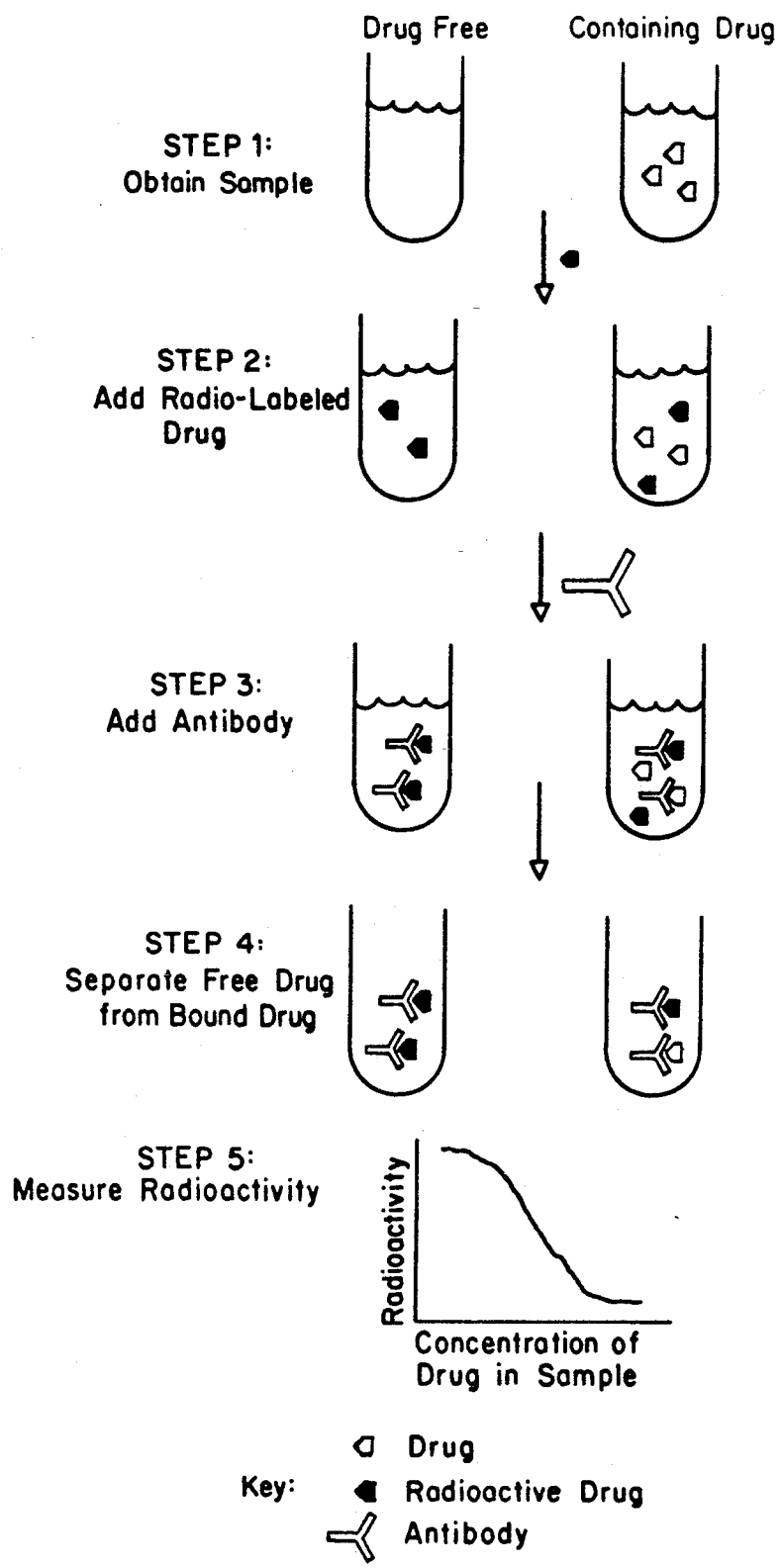
FIG. 1 shows steps used in a radioimmunoassay.

The principles of a competition immunoassay, wherein antibodies are used as the binding species, are outlined in FIG. 1. In the example of FIG. 1, the small molecular weight species is cocaine. Compare two cases where a sample contains or does not contain cocaine. In step one, a measured amount of sample is obtained. To this sample, a radioactive form of cocaine is added. Then, antibodies that are specifically designed to recognize cocaine, are introduced in an amount just sufficient to bind all the labelled cocaine. The antibodies cannot distinguish between the cocaine that may be present and the radioactive form of cocaine added. Thus, the antibody may bind to either form of cocaine. In this competition for the binding sites on the antibody, if there is a large amount of unlabeled cocaine in the sample, then the probability of the labeled drug becoming bound to the antibody is reduced. If there is no unlabeled cocaine in the sample, then all of the labeled cocaine would become bound to the antibody. Then, the unbound cocaine (radio-labelled or not) is separated from that bound to the antibody by any number of techniques. The remaining radioactivity bound to the antibody is then measured. The intensity of this radioactivity is inversely proportional to the amount of unlabelled cocaine in the original sample.

The method according to the present invention relies on a label which varies the wavelength dependance of its spectra (either emission, transmission, or absorbance) depending upon its concentration. An example of such a molecule is pyrene and its derivatives.

As shown in FIGS. 3a and 3b, pyrene possesses different fluorescent spectra at high and low concentrations. At high concentrations two pyrene molecules are close enough for the pi-systems to overlap. It is well-known that the interaction of the pi systems causes emission of light having an emission maximum at a longer wavelength (~480 nm). At low concentrations the pyrene molecules are too far apart for two pyrene molecules to interact and only an emission at 378 and 396 nm is observed. Thus, the ratio of light emitted at 378 and 396 nm to 480 nm is a measure of the concentration of pyrene in the sample.

Figure 2:
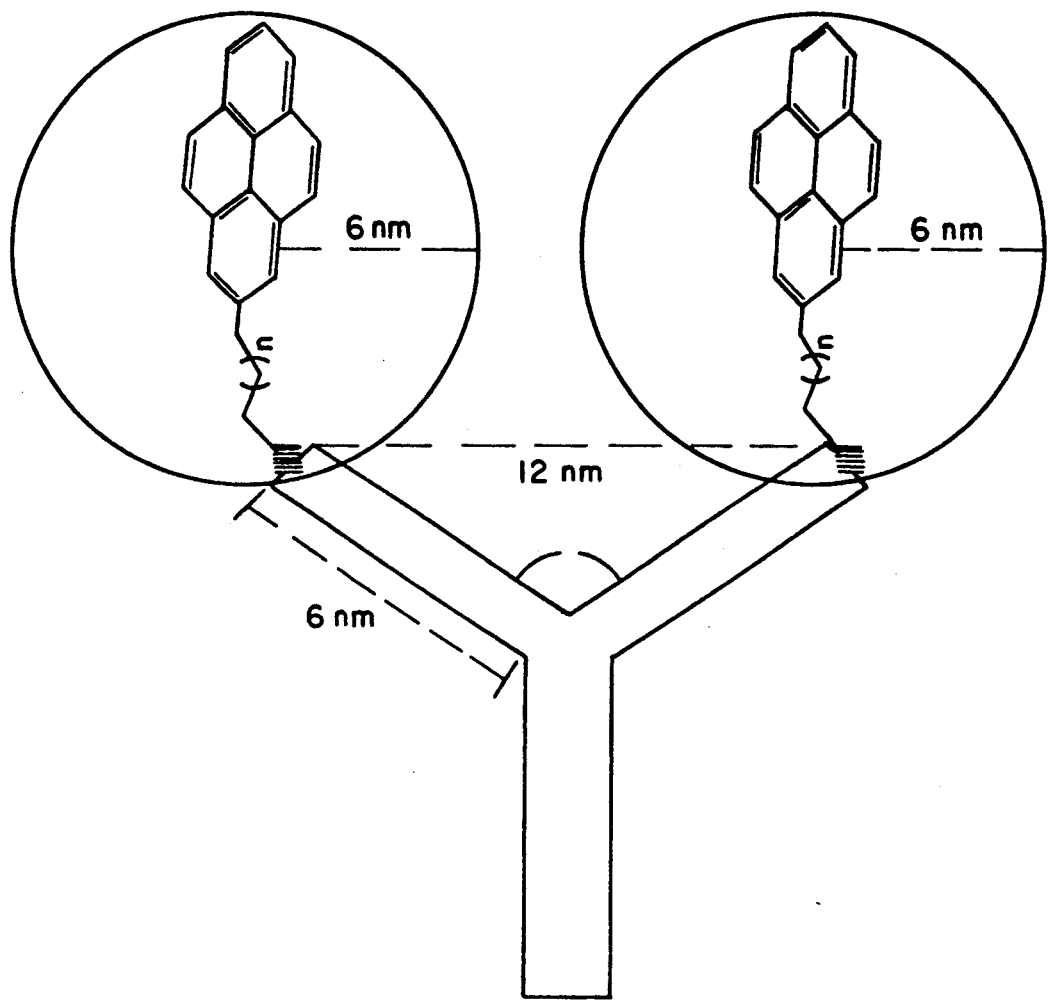
FIG. 2 shows the calculation for the effective concentration of two pyrene molecules bound to an antibody through a linker arm.

It is not generally recognized that molecules can be brought into close proximity to each other by binding with other molecules. The effective concentration of molecules is a calculated value that describes what concentration would need to be prepared to provide a solution in which the molecules are a given average distance apart. For example, as schematically shown in FIGS. 2, two molecules of pyrene are bound via a linker arm to an antibody molecule. These pyrene molecules are approximately 12 nm apart. One would have to prepare a solution that was $1.8 \times 10^{-3}$ M in pyrene for the molecules to be an average of 12 nm apart. Therefore, the effective concentration of these bound molecules is defined as $1.8 \times 10^{-3}$ M. The effective concentration of these molecules (two or more molecules bound to a third) is independent of the macroscopic concentration. In other words, if one were to take one of these complexes of molecules and place it in one liter of water, the effective concentration would remain the same, i.e., $1.8 \times 10^{-3}$ M, whereas the actual concentration would be $1/(6.02 \times 10^{23})$ or $1.6 \times 10^{-22}$ M, a very small value. Pyrene shows a substantial excimer at actual concentrations greater than $10^{-3}$ M. In FIG. 2, for the pyrene molecules to show a change in spectra that would correspond to an effective concentration of $1.8 \times 10^{-3}$ M, they must be able to interact with each other. Thus, the linker arm shown schematically in FIG. 2 is essential for the interaction to occur. If the antibody, also shown schematically in FIG. 2, were a rigid structure and the distances were as shown in FIG. 2, the linker arm would have to be at least 6 nm long for the pyrene molecules to come into contact. The effective concentration determines the shape of the emission spectrum, whereas the actual, or absolute, concentration of the fluorophore determines the intensity of emission.

This definition of effective concentration is also applicable to the prior art energy-coupling schemes, although these schemes operate on different principles than does the present invention. In the present invention, the labels must approach each other at extremely close distance so that an electronic interaction which alters the available energy levels of the light-emitting electrons occurs. In energy-coupling schemes, energy transfer takes place, but the available energy levels of the light-emitting electrons do not change. A significant advantage of the present invention over chemiluminescent energy transfer is that the bound and unbound fluorophores may be repeatedly probed, since the change in available energy levels, when averaged over a plurality of molecules, is stable over time. On the other hand, chemiluminescence is a transitory phenomenon and must be measured instantaneously, since the energy produced is quickly dissipated. Another advantage of the present invention over acceptor/donor energy transfer is that the present invention has no problem with the overlap of the excitation bands of the donor and acceptor, since no energy transfer is involved.

The principle behind the present invention, which, in a preferred embodiment, is referred to as PORSCHA, for Pi Overlapping Rings Systems Contained in a Homogeneous Assay, is shown, in FIG. 3a through 3d. In this case "homogeneous" refers to an assay where no separation steps are necessary, even if the system may or may not a single phase. In this binding assay, antibodies can bind to two molecules at a time. If the antibody binds to two of the pyrene-labeled antigens or haptens (FIG. 3a), then it will have brought the two separate molecules closer together. Therefore, the effective concentration is much higher than the actual concentration as discussed above. In this instance, the spectra would show an excimer (FIG. 3c). On the other hand, in FIG. 3b, if one or both of the binding sites on the antibody were occupied by unlabelled hapten, then either no or only one pyrene-labelled hapten could bind. Thus, the effective concentration would equal the actual concentration, which is very low. Therefore, no excimer would be observed (FIG. 3d). That is, for the effective concentration to differ from the actual concentration, two or more labelled molecules must be bound in close proximity. Of course, if the actual concentration is very high (in the case of pyrene, greater than $10^{-3}$ M), the spectrum would show very little change between the bound and unbound states. However, very few binding assays are performed at these high concentrations.

Pyrene and closely related pyrene derivatives (structures containing the four-membered ring system characteristic of pyrene) are the best choices for indicators according to the present invention because they show strong differences in fluorescent spectra with concentration and have long fluorescent lifetimes if time-resolved spectroscopy is used to resolve background interferences. Other compounds which show similar change spectral absorption or emission maxima dependant upon concentration may also be used. In general, polycyclic aromatic compounds, such as napthalene, perylene, and various fluorescent dyes, such as acridine orange, may be used as labels according to the present invention.

The spectral change can be observed by various means. For example, the emission spectra of the label can be measured after excitation with any form of energy, such as electromagnetic radiation, heat, particle radiation, or chemical energy (chemiluminescence). Alternatively, the spectral absorbance of the label can be monitored, although decreased sensitivity would be expected.

The indicator may be attached to the antigen by any of various known methods using an organic linker. The linker arm is preferably about 20 to about 100 carbons long, depending on the structure of the binding molecule. For example, with streptavidin, one can use a linker arm which is five atoms long (FIG. 6, compound C3), whereas a closely related molecule, such as avidin, requires a much longer linker arm, for example PEG400, shown in FIG. 4. If the linker arm is too short, the pi rings of the labels will not interact. If the linker arm is extremely long, the indicators will possess too may degrees of freedom to insure proper overlapping and thus the spectral change would be reduced. However, the length requirement past a given length is quite broad, since anything between 5 and 229 atoms has been shown to work for streptavidin. Likewise, Cuniberti et al., Eur. polymer J. pp 887 to 893 (1980) show that two pyrene molecules may be linked with long linkers (1,300 bonds) and still exhibit excimer formation.

The linker is preferably water-soluble and flexible. Examples include, but are not limited to, polyethylene oxides, polyamino acids, polyamides, and DNA. The only requirements are matrix-solubility at the concentration used and appropriate length.

In performing an assay according to the present invention, a buffer is needed to both dilute the components and provide an environment in which the binding of the tracer can occur. Many types of buffers may be employed, including those containing protective proteins, such as bovine serum albumin, gelatin and casein. A number of surfactants above and below their critical micelle concentration such as sodium dodecyl sulfate, TRITON X-100® (a non-ionic polyethylene oxide-based grafted on an octylbenzene), TWEEN 20® (a non-ionic polyethylene oxide grafted to polysorbate) and trimethylhexadecylammonium bromide may be used to potentially reduce non-specific binding of the label to the walls of the measurement system or other artifacts within the measurement matrix. However, in the experiments performed to date, non-specific binding in the absence of surfactant does not appear to be problematic. The excimer intensity varies depending upon the surfactant and is maximal with SDS, below its critical micelle concentration, or without any surfactant.

The binding assay according to the present invention is also useful with inorganic or organic surfaces having specific binding sites for two or more other molecules. For example, the coverage and mobility of molecules on gold surfaces could be measured by exposing the surface to a solution containing an appropriate label, such as pyrene or a derivative thereof, attached to a thiol. Such a labelled material will bind to the gold surface through the thiol functionality only if the surface has free binding sites. If the surface had been previously covered with other thiols, no other binding would occur only if one of these thiols can be displaced in the chosen matrix. Thus, a measurement of the surface coverage, mobility, and ease of displacement of thiols on a gold surface can be made without removing the surface from the matrix solution. Also, in a given system with a known actual concentration of binding sites and a specified label and linker arm, the intensity of the spectral change varies with the distance between the binding sites. Likewise, the minimum distances between binding sites on an uncharacterized molecule or surface may be determined by varying the linker arm length and determining the minimum length of linker arm which results in a spectral change. Thus, the method of the present invention can be used to determine the distance between binding sites for surfaces and for biomolecules.

The binding sites may be on a substance which is composed of two or more molecules in a fixed or oriented spatial relationship such that the average distance between the molecule remains about constant. For example, antibody fragments (such as Fab) can have only one binding site, but these fragments can be oriented by binding to secondary antibodies to provide two binding sites on the complex. Alternatively, these fragments can be oriented by attachment to a surface. Although such an assay would contain two phases, no separation steps would be required to detect the signal change and therefor it would be considered homogeneous within the context of the present invention.

The assay according to the present invention can be performed in aqueous or non-aqueous media. Typically, the matrix within which bioassays according to the present invention is performed is aqueous-based. However, molecules such as antibodies have been shown by others to selectively bind other molecules in substantially non-aqueous media, such as air.

Figure 12:
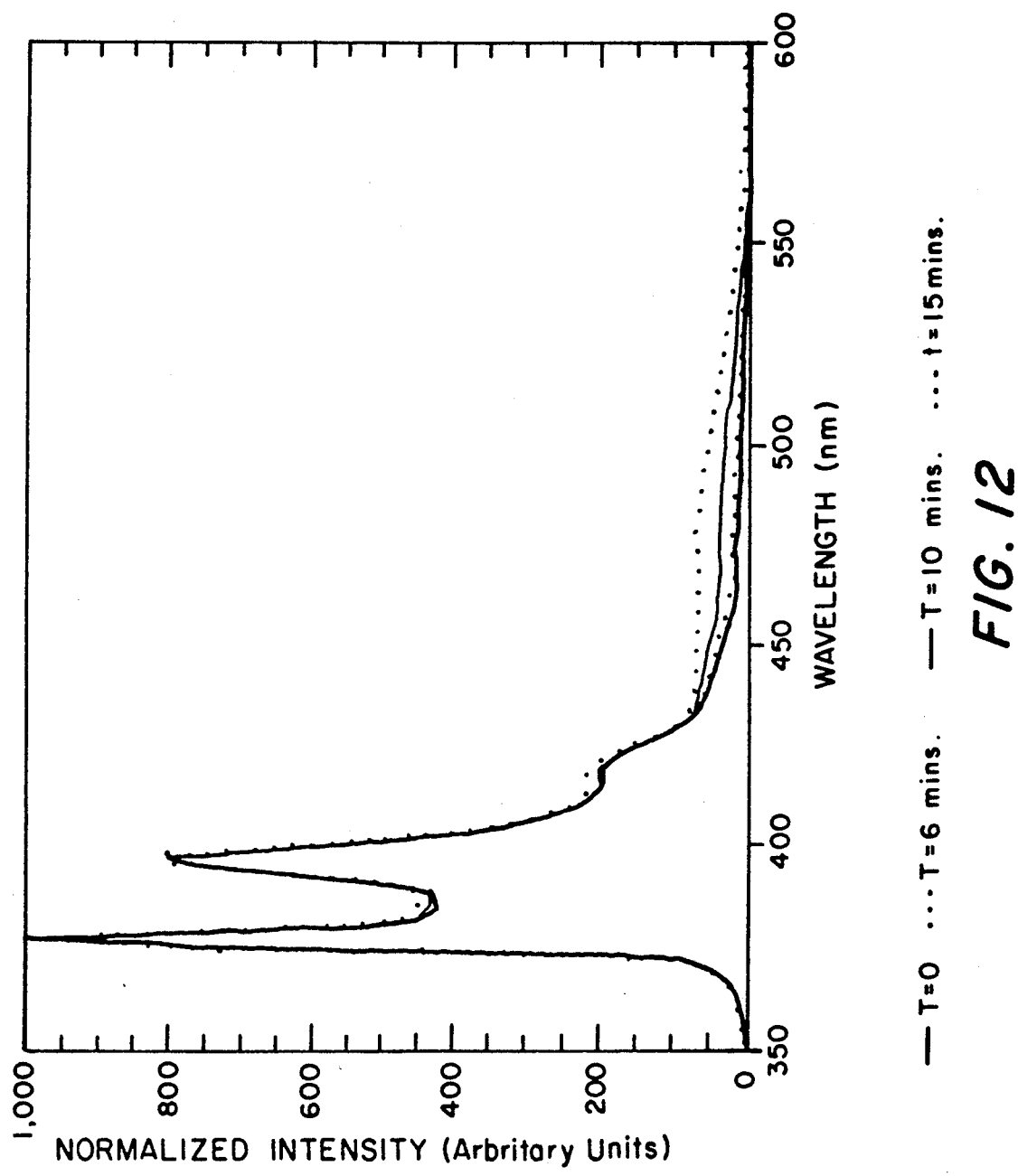
FIG. 12 shows that an antibody will elicit an excimer with the appropriate linker arm and sufficient time for equilibrium to occur.

The results with the antibodies shown in FIG. 12 require great care to obtain. In particular, antibody assays according to the present invention, as opposed to other binding assays, are particularly sensitive to variations in methodology, such as time, concentration, reagent purity and temperature.

Having described the invention, the following examples are given to illustrate specific applications of the invention including the best mode now known to perform the invention. These specific examples are not intended to limit the scope of the invention described in this application.

EXAMPLES

EXAMPLE 1

The Detection of Cocaine

4-Carboxypyrene butyric acid was synthesized using the method of Cook and Hewett (J. Chem Soc., 398(1933), incorporated herein by reference). The carboxyl group was removed by the method of Huang-Minlon (Huang-Minlon, J. Amer. Chem. Soc., 71 3301(1949), incorporated herein by reference). The product, pyrene butyric acid (PBA) was purified by the procedure outlined in Cook and Hewett (J. Chem. Soc., 398(1933)).

PBA was conjugated to polyethylene glycol (PEG) by the following procedure. PBA was activated by 1,1'-carbonyldiimidazole (CDI) in dioxane. Then excess PEG was added. The solution was heated at 60° C. for two hours. Water was added to remove the excess PEG and the PEG-PBA conjugate was extracted into chloroform. Benzoylecgonine (a cocaine derivative) was also activated with CDI. The activated benzoylecgonine was added to the PEG-PBA conjugate, which was allowed to react for several days.

When the synthesis of the pyrene-cocaine conjugate was completed, the impure product was purified by High Pressure Liquid Chromatography (HPLC). Fractions were collected at various times and were analyzed with a commercial immunoassay to determine which fraction contained the benzoylecgonine-PEG-PBA conjugate.

The collected fractions were tested on an SLM-8000 spectrofluorometer. The excitation wavelength was set at 343 nm. The emission was scanned from 350 nm to 600 nm in steps of 2 nm with an integration time of 1 sec. All slits were set to 4 nm. A 200 μl quartz cell was used.

The monoclonal antibodies were obtained from either Roche Diagnostic Systems, Nutley, N.J. lot 18008-08-09079 or ImmunoSearch, Inc., Toms River, N.J. The antibodies were diluted 1:5 in phosphate buffered saline (PBS), pH 7. The collected fractions were also diluted by a factor which ranged from 1:10 to 1:50. 100 μl of the diluted fractions were then put into the cell. After data was collected, 2-5 μl of antibody was added and another spectral measurement was obtained. Then, after a 5 minute delay, 5 μl of cocaine was added to the cell. Again, a spectral measurement was recorded. After the last spectra, there was usually a 5-10 minute interval before another spectral measurement was taken.

In the initial solution, the pyrene labeled cocaine (benzoylecgonine, a derivative of cocaine) is too dilute to observe any emission at ~480 nm. When antibody is added to the sample containing cocaine and pyrene labeled cocaine, either will bind to the antibody. If both binding sites of the antibody were occupied by the pyrene labeled cocaine, then the double peak spectra would be seen. If there was free cocaine in the sample, then it would displace either both or one of the labeled cocaine molecules. Thus one peak would be observed rather than two. When both binding sites are occupied by the labeled cocaine, then the pyrene molecules would have a chance to come closer together, thus mimicking a high concentration solution (FIG. 3). If a free cocaine molecule occupied even one of the binding sites, this situation would mimic a dilute solution producing only one emission at 396 nm. Thus, the ratio of 480 nm to 378 and 396 nm would be inversely proportional to the cocaine concentration of the given sample.

Calculations showed that a distance of 42 carbon atoms was optimal for the overlap of two molecules bound to an antibody. Therefore, pyrene butyric acid was linked via a polyethylene glycol chain to benzoylecgonine (a cocaine derivative) to provide at least the 42 carbon chain (see FIG. 4) required. Polyethylene glycol (PEG) was chosen because of its ready availability in different chain lengths. To test this assay, a mixture of chain lengths was employed. Too short a chain length does not allow the two pyrene conjugates to come into contact and hence no excimer results. Too long a chain length decreases the chance that the two pyrene molecules would come into contact and this would result in a decrease in the excimer intensity.

EXAMPLE 2

Testing Using Streptavidin as Antibody Mimic

The principle of the present invention as an assay for a substance in urine was simulated by the determining the effect of concentration of biotinylated pyrene in the presence of another binding compound, streptavidin, on the fluorescent spectrum of the biotinylated pyrene. Pyrene was biotinylated, using conventional techniques, via an amido linker arm, —OC—HN—X—NH—, to a molecule of biotin. The resulting biotinylated biotin was very carefully purified, by conventional techniques, to remove any free biotin.

EXAMPLE 3

Preparation of the EDR148 Linker (FIG. 4)

To a 20 ml vial was added 50 mg of pyrene butyric acid N-hydroxy succinimide (PBA-NHS), 5 ml of methylene chloride and 200 mg of JEFFAMINE ® EDR-148 (Texaco) (about 10 fold molar excess), a polyethylene oxide diamine of MW 148. The reaction was allowed to occur overnight at room temperature. Then, the solvent was removed by blowing an air stream into the vial. The residue was dissolved in water and applied to a $C_{18}$ solid phase extraction cartridge which was prewet with methanol and then water. The pyrene derivative collected as a band, highly fluorescent in the blue region, at the top of the cartridge. The cartridge was washed extensively with water to remove unlabelled EDR-148 and the pyrene derivative eluded with methanol. The methanol was removed by evaporation under an air stream and replaced with dimethylformamide. Excess (about 2 to 5 times) biotin N-hydroxysuccinimide molar over the linker was added. The reaction was allowed to occur over a two-day period at room temperature. Then, the solution was applied in portions (about 4 portions) to 20×20 cm silica preparative TLC plates, one portion per plate. The plate was developed with 90% chloroform, 10% methanol. The product band (blue fluorescence) was scraped off the plate and the product was removed with methanol. Portions (about 100 μl out of 10 ml of methanol solution) of these were further purified on a C18 HPLC column using a 0 to 100% acetonitrile-0.1 M ammonium acetate gradient and monitoring the effluent with a fluorimeter. Fractions were collected when the fluorimeter indicated elution of the pyrene labelled material. HPLC was performed to remove potentially free biotin. It may be unnecessary to use HPLC if the thin layer chromatography is sufficient to remove all the free biotin. The other labelled biotin molecules shown in FIGS. 4 and 5 were prepared in an analogous manner.

EXAMPLE 4

Use of the EDR148 Linker of Example 3

Figure 6:
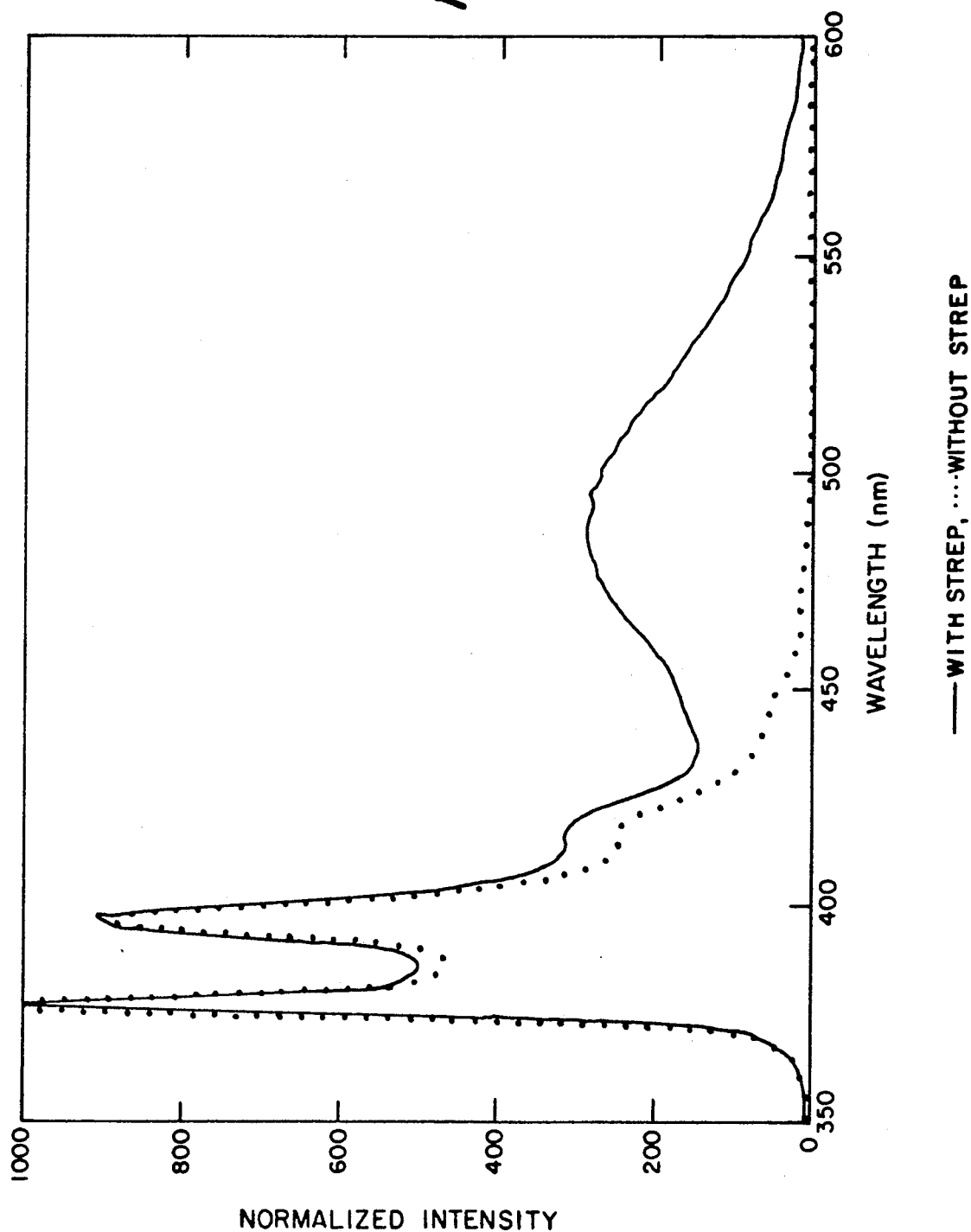
FIG. 6 shows two fluorescent spectra of linker EDR192 with and without streptavidin present, demonstrating production of an excimer. The spectra were normalized to the base peak at 378 nm.

If an insufficient concentration of the binding molecule (in this case streptavidin) was used, the excimer would not be at a maximum. Likewise, if too much binding molecule is used, the excimer also will decrease, since on an average, the two binding sites would not be occupied simultaneously. Thus, a balance between the labelled biomolecule and its corresponding binding material is needed. The resultant HPLC purified material of Example 3 was titrated with dilute solutions of streptavidin such that a maximal intensity of the excimer resulted. An example of the spectrum of an excimer produced is shown in FIG. 6. In this Figure, the spectra without streptavidin and with streptavidin is depicted. Both spectra are normalized to the base peak intensity at 378 nm. Otherwise, the spectra with streptavidin would have less absolute fluorescent intensity since the fluorescent intensity is spread over both the monomer and excimer peaks.

EXAMPLE 5

Computer Simulation of PORSCHA and RIA

A computer program was written to perform the following tasks:
1. A matrix is filled with a thousand "1"'s, which represent a thousand labelled molecules.
2. The computer selects from this matrix, 500 pairs at random, without replacement and then examines both components of the pair. If these components are both "1"'s, then the computer would consider an "excimer" to be produced. If either component is a "0", which represents an unlabelled molecule, then an excimer would not be produced. During the selection process the computer keeps track of the number of excimers found.
3. In the next step, increasing numbers of "1"'s are replaced with "0"'s (unlabelled molecules) and the selection process described in step two is repeated.

Figure 7:
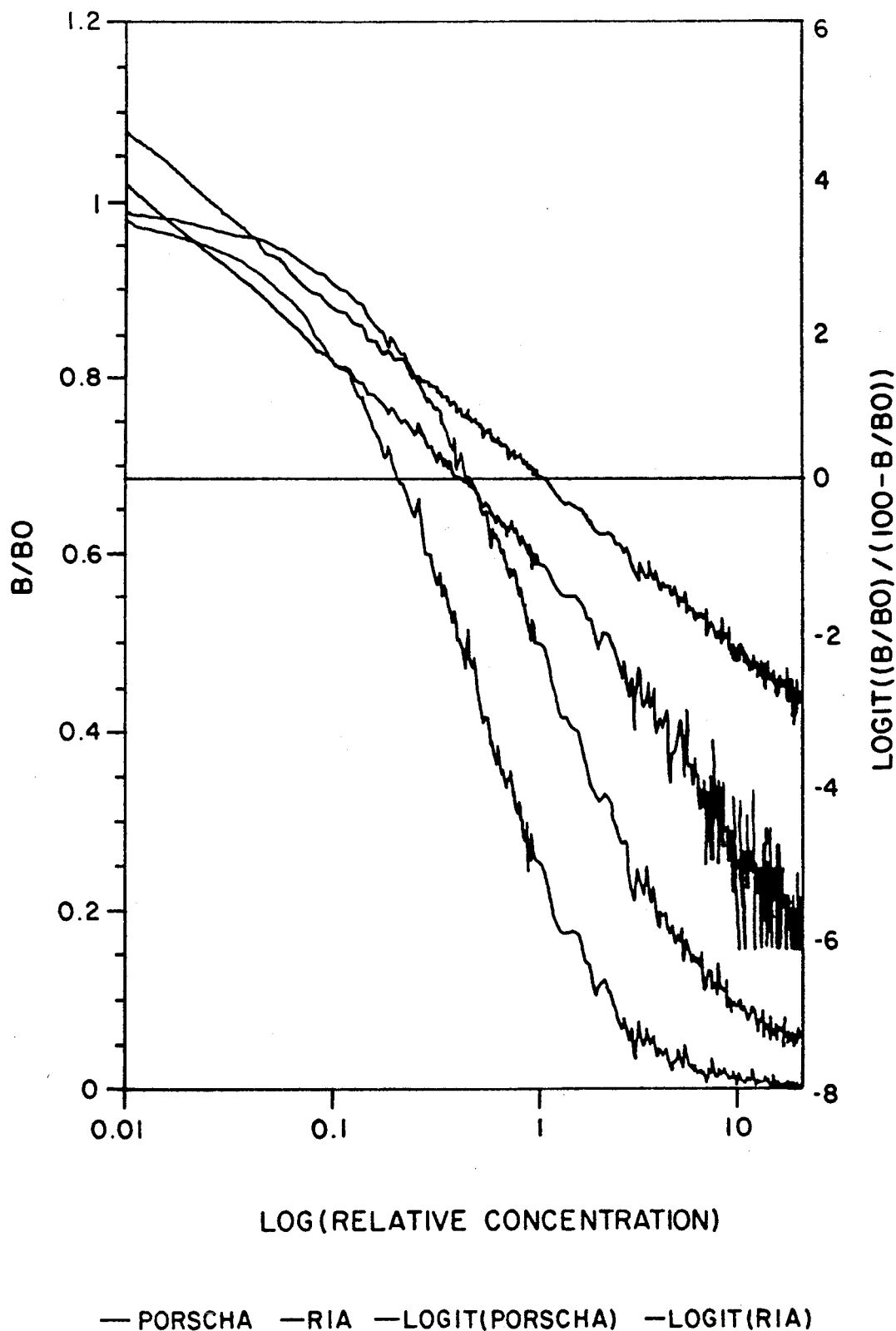
FIG. 7 is a computer simulation of PORSCHA vs. RIA showing increased sensitivity of PORSCHA at low concentrations compared to RIA. Also, the characteristic sigmoidal curve or RIA is generated by PORSCHA.

In the first pass through the program, since only "1"'s are present, 500 excimers would be counted. As the ones are replaced by "0"'s, decreasing numbers of excimers are produced. For RIA, a very similar scheme is used, except that a label is considered present if either of the molecules selected in step two are "1"'s. The results of such a simulation are depicted in FIG. 7. As can be seen, the S-shaped curve for PORSCHA is shifted to the left relative to RIA. This indicates that PORSCHA gives a larger signal difference for lower concentration species than does RIA. A linear line may be generated from both curves through the use of the logit function. The "noise" depicted in FIG. 7 is the result of the limited number of points in the matrix and the random nature of the selection process.

EXAMPLE 6

Generation of Binding Curve for EDR148 Linker and Streptavidin

Figure 8:
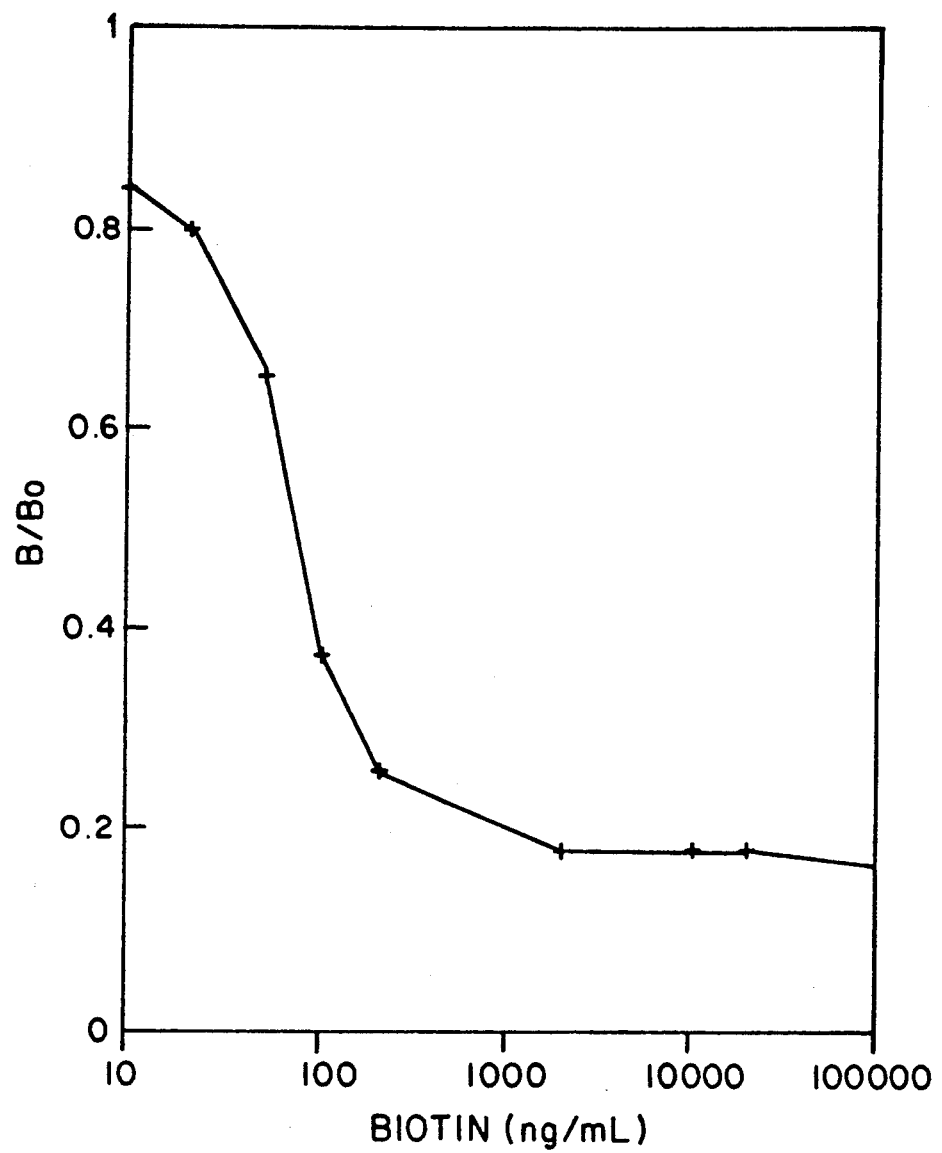
FIG. 8 is a curve demonstrating the sigmoidal curve modelled in FIG. 7. The ratio of excimer to monomer areas is plotted with increasing concentration of unlabelled biotin added to the solution.
Figure 11:
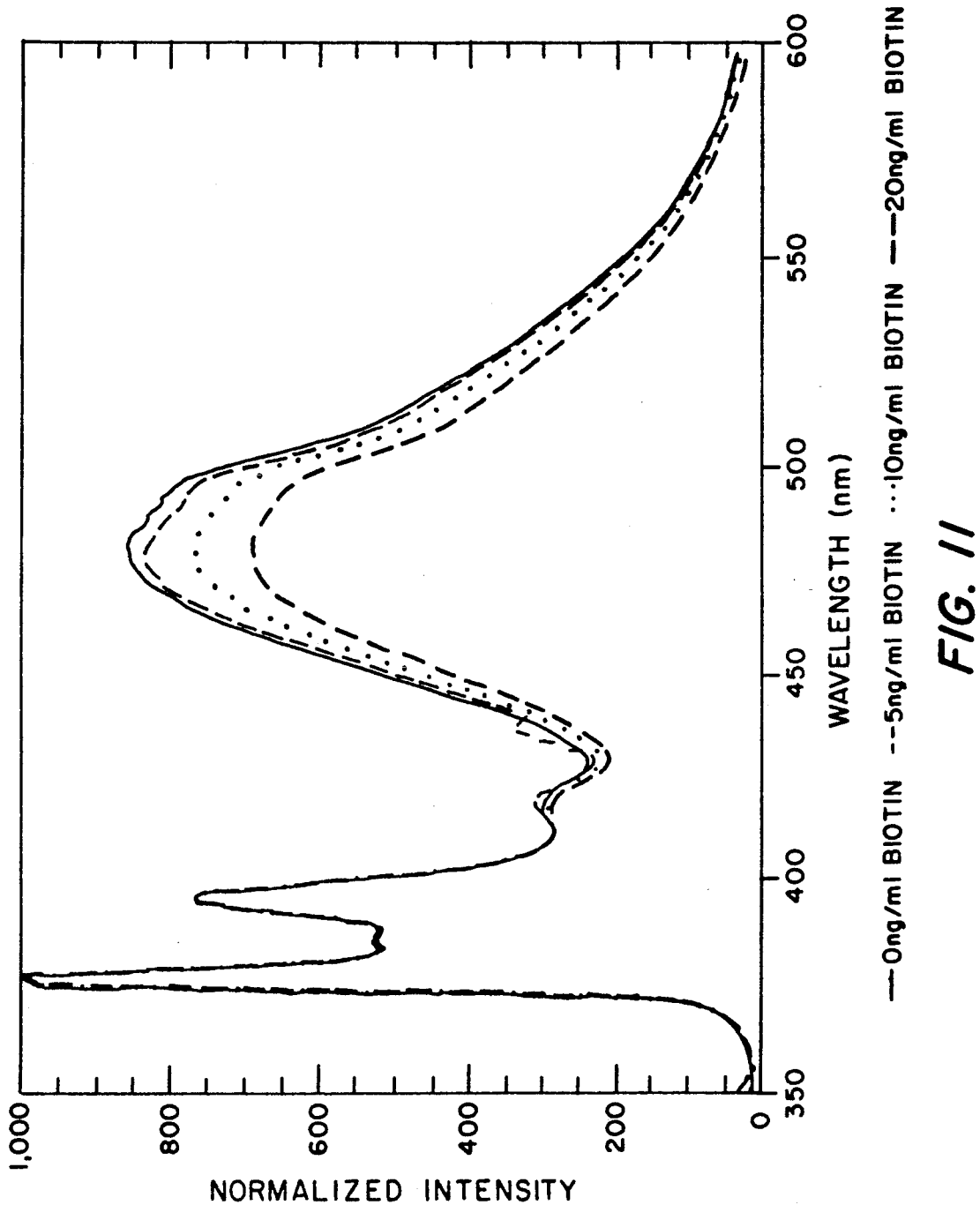
FIG. 11 shows the change in excimer intensity with increasing free biotin in solution. All spectra were normalized to one at 378 nm.

Streptavidin has a very high binding affinity for biotin. This binding affinity implies that the initial binding event occurs very rapidly and that the displacement of the bound biotin molecule occurs very slowly. Thus, to generate a binding curve, one has to carry out a series of experiments rather than just adding free or unlabelled biotin. Solutions of biotin in phosphate buffered saline (PBS) containing 2.5% w/v sodium dodecylsulfate (SDS) were prepared, then 5 μl of these solutions were added to a cuvette containing the optimized EDR148 linker from Example 3 in 100 μl of PBS with SDS. After mixing, the optimal streptavidin concentration, as determined in Example 4, was added and the spectra recorded. These steps were repeated for varying biotin concentrations. The area under the several wavelength ranges corresponding to the monomer and excimer fluorescent bands was calculated and the ratios plotted in FIG. 8 to generate the S-shaped curve. The raw data used to generate this Figure is similar to that shown in FIG. 11. The raw data shown in FIG. 11 was obtained by the same method used to obtain the raw data employed to generate FIG. 8. The curve of FIG. 8 has the characteristics predicted by the computer simulation of Example 5 and demonstrates that the excimer to monomer ratio changes with biotin concentration and can be readily detected.

The position of inflection of the S-shaped curve is determined by the concentrations of label and binding molecule. The curve may be shifted to the left (made more sensitive) by decreasing the concentration of both species. Likewise, the curve may be shifted to the right (made less sensitive) by increasing the concentration of both species. The limit of sensitivity is determined by at least three factors:
1. The binding constant of the binding molecule.
2. The fluorescent background of the matrix.
3. The sensitivity for detection of the fluorescence emitted.

EXAMPLE 7

Fluorescent Background Interferences Observed by Some Environmental Matrices

To obtain maximal sensitivity, the binding molecule and the labelled species must be in as low a concentration as possible. In this manner, small quantities of unlabelled compounds can occupy the majority of binding sites on the binding molecule or species and produce the largest signal difference. However, many environmental matrices possess species with fluorescent properties that can mask the label. At least two methods exist to reduce or eliminate these interferences. One is to take background spectra before the labelled tracer is added in Example 6. Another would be to use time-resolved spectroscopy to take advantage of the long fluorescent lifetime of pyrene. However, the instrumentation to use the latter technique is more expensive than background subtraction, so background subtraction was chosen to demonstrate PORSCHA in real matrices.

Figure 9:
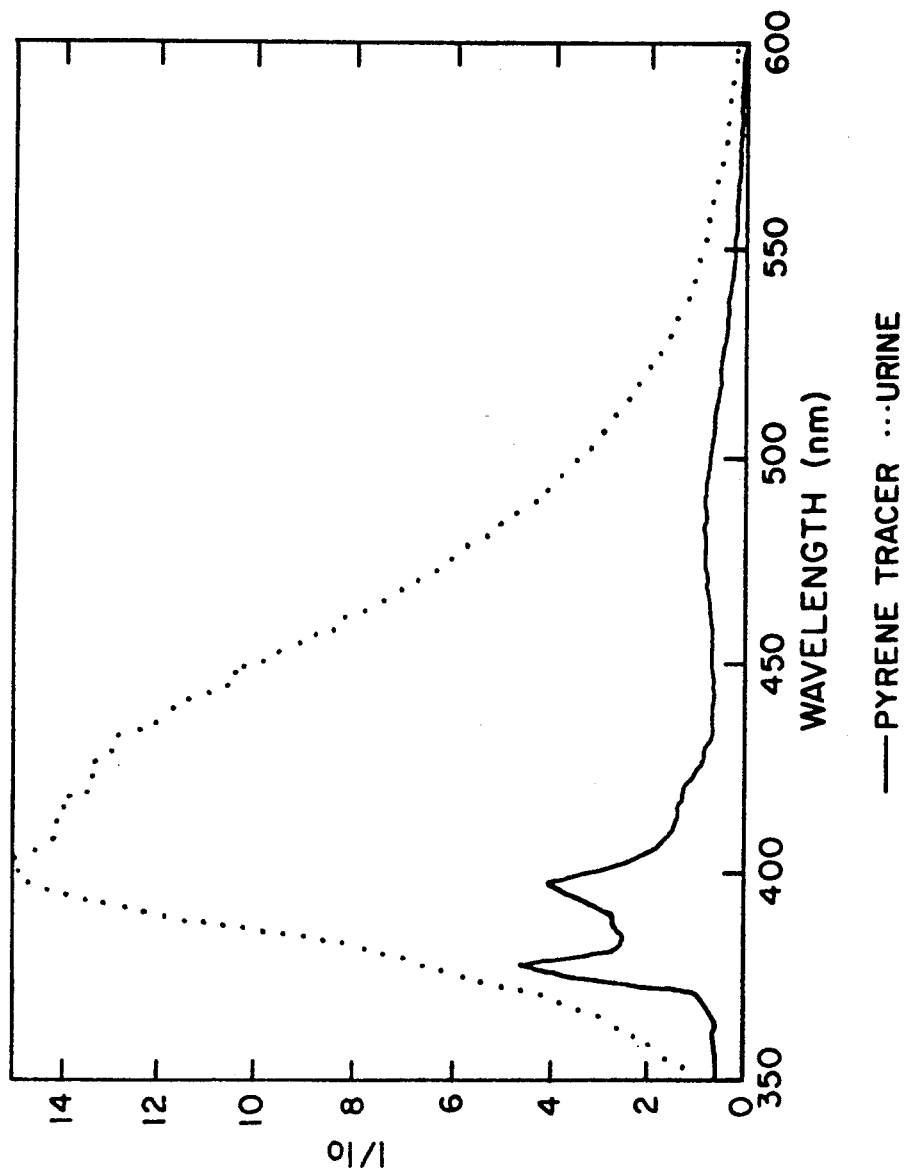
FIG. 9 shows the interference of endogenous fluorescent materials in some biological media such as urine. This interference may be overcome by either careful background substraction or by use of time-resolved fluorescent spectroscopy to take advantage of the long fluorescent lifetime of pyrene compared to most endogenous fluorescent materials.

FIG. 9 shows the fluorescent background typically produced by urine, using dotted lines. The solid line shows the labelled pyrene in PBS, a matrix without substantial fluorescence. Although this ratio of background to signal is sufficient to generate reasonable precise data, a higher concentration of label, where the fluorescence is at least as intense as the background fluorescence, is desirable for background substraction.

Figure 10:
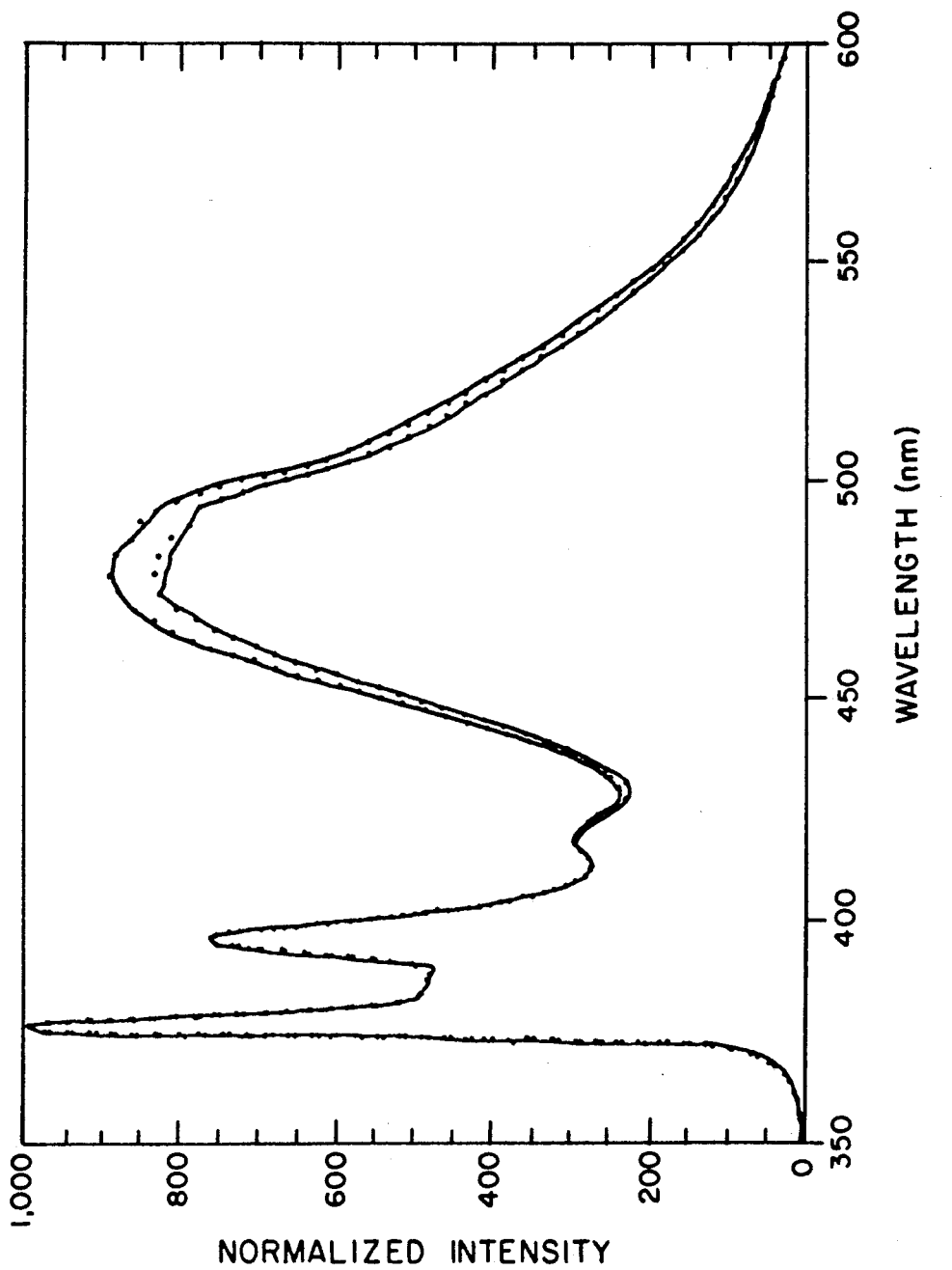
FIG. 10 shows several background-subtracted spectra demonstrating the reproducibility of spectral subtraction with 0 and 5 ng of free biotin per cuvette. The buffer has minimal fluorescent background whereas the background in urine is substantial as shown in FIG. 9.

Using the general procedures of Example 6, increasing the volume of the cuvette to ~2 ml while keeping the concentrations of the various system components as in Example 6, 5 $\mu$l of urine was substituted for some of the PBS to prepare the standard concentrations of biotin, using about four times the concentration of pyrene label as used in FIG. 9. In the cuvette is about $2.2 \times 10^{-11}$ moles of streptavidin, about $7.15 \times 10^{-11}$ moles of biotin derivative, and for the 5 ng of biotin in the cuvette, about $2 \times 10^{-11}$ moles of biotin would be present. FIG. 10 shows four spectra. Two of these spectra shown by the solid lines were obtained in PBS, where fluorescence of the matrix is minimal. The other two, shown by dotted lines, were obtained in urine, where the fluorescence of the matrix is substantial. The substantial correspondence of the two pairs of curves demonstrates that background subtraction is a viable method for reducing interferences from the matrix.

EXAMPLE 8

Demonstration of Excimer Production with an Antibody and Appropriate Linker Arm (EDR192L)

Goat anti-biotin was added to a solution of the linker in PBS with SDS as in Example 6, using linker arm PBA-EDR192L-Pro-Bio (FIG. 5). The change in spectra with time was monitored and the production of an excimer was noted, as shown in FIG. 12. Since antibodies have lower binding constants than streptavidin, a longer equilibrium time must be used before recording the spectra. FIG. 12 demonstrates that an appropriate linker arm can generate an excimer with an antibody. This linker arm has a bend (in this case ~120°) incorporated in its structure because of the proline functionality. This bend is needed to produce substantial excimer formation because of the tertiary structure of the antibodies employed. With current bioengineering technology, molecules which recognize and bind other molecules can be produced in bacteria (Pack et al., Biochemistry, 31, 1579 (1992)). These bio-engineered molecules are likely to have structures different from conventional antibodies. If the binding sites are closer to each other than in conventional antibodies, a bend may not be necessary in the linker structure. Interestingly enough, this linker (EDR192L) works poorly with streptavidin compared to the corresponding linker without the proline.

Obviously, many modifications and variations of the present invention are possible in light of the above teachings. It is therefore to be understood that, within the scope of the appended claims, the invention may be practiced otherwise than as specifically described.

What is claimed is:

1. A method for detecting the presence of a substance having binding sites for at least two molecules, in a sample suspected of including said substance, comprising the steps of:

adding to the sample which specifically binds said at least two binding sites of the substance and which is attached to a polycyclic aromatic label wherein, when at least two of said labelled molecules bind to said at least two binding sites, said labels of said two labelled molecules electronically interact with each other to form an excimer and thus vary the wavelength dependance of their spectra; and determining whether said excimer has formed by detecting any said variation int he spectra of the label;

wherein detection of said variation of said spectra of the label indicates the formation of said excimer and the presence or absence of said substance in said sample.

2. The method of claim 1, wherein said variation occurs in the emission spectra of said labels.

3. The method of claim 1, wherein said variation occurs in the absorption spectra of said labels.

4. The method of claim 1, wherein the substance is an antibody or antibody fragments oriented such that said two or more binding sites are insufficiently close proximity for said binding of said two said labelled molecules to said at least two binding sites to form said excimer.

5. The method of claim 1, wherein the substance is a receptor.

6. The method of claim 1, wherein the substance is a surface that specifically binds said at least two molecules.

7. The method of claim 1, wherein the labelled molecule comprises a label, a linker and a moiety which recognizable by said at least two binding sites.

8. The method of claim 7, wherein the sample is a liquid, said linker is soluble in said liquid and is between 1 and 1,300 atoms long.

9. The method of claim 8, wherein the linker has a bend within it which is sufficient to form a substantial amount of said excimer in said sample when said labelled molecule is bound to said at least two binding sites.

10. The method of claim 1, wherein the substance is straptavidin or avidin and said labelled molecule is biotinylated.

11. The method of claim 1, wherein the label is a fluorescent dye.

12. The method of claim 1, wherein the label includes a pyrene ring, a napthalene ring to an anthracene ring.

13. The method of claim 1, wherein the sample includes a surfactant.

14. The method of claim 1, wherein said detection step comprises the steps of exciting the label and measuring light emission at least at one wavelength where the spectral emission of said label is changed by the formation of said excimer.

15. The method of claim 2, wherein said detection step comprises the step of measuring the spectral emission of said label at least at one wavelength where the spectral emission of said label changes upon the formation of said excimer.

16. The method of claim 1, wherein said polycyclic aromatic label is acridine orange.

17. The method of claim 1, wherein said matrix is aqueous.

18. A competition assay for detecting the presence of a substance in a sample suspected of including said substance, comprising the steps of:

adding to the sample a molecule which is attached to a polycyclic aromatic label;

contacting said sample containing said molecule with an antibody having at least two binding sites, each of which specifically binds both the substance and said labelled molecule, wherein, when at least two of said labelled molecules bind to said at least two binding sites, said labels of said two labelled molecules electronically interact with each other to form an excimer and thus vary the wavelength dependance of their spectra; and determining the amount of excimer that has formed by detecting any said variation in the spectra of the label, wherein the amount of excimer formed is inversely proportional to the amount of said substance in said sample.

19. The method of claim 18, wherein said substance is cocaine.

* * * * *